United States Patent [19]

Bowlin

[11] Patent Number: 5,308,837
[45] Date of Patent: May 3, 1994

[54] 5'-AMINE SUBSTITUTED ADENOSINE ANALOGS AS IMMUNOSUPPRESSANTS

[75] Inventor: Terry L. Bowlin, Maineville, Ohio

[73] Assignee: Merrell Dow Pharmaceuticals Inc., Cincinnati, Ohio

[21] Appl. No.: 975,211

[22] Filed: Nov. 12, 1992

Related U.S. Application Data

[63] Continuation of Ser. No. 840,658, Feb. 20, 1992, abandoned, which is a continuation of Ser. No. 571,042, Aug. 22, 1990, abandoned.

[51] Int. Cl.$^5$ .............................................. A61K 31/70
[52] U.S. Cl. ...................... 514/46; 514/825; 514/866; 514/885; 514/903
[58] Field of Search ............... 514/46, 825, 866, 885, 514/903

[56] References Cited

U.S. PATENT DOCUMENTS

| | | | |
|---|---|---|---|
| 3,666,856 | 5/1972 | Elion et al. | 514/46 |
| 3,758,684 | 9/1973 | Elion et al. | 514/46 |
| 4,081,534 | 3/1978 | Elion et al. | 514/46 |
| 4,309,419 | 1/1982 | Wolberg et al. | 514/46 |
| 4,481,197 | 11/1984 | Rideout et al. | 514/46 |
| 4,704,381 | 11/1987 | Schaumann | 514/46 |
| 4,912,092 | 3/1990 | Gruber | 514/45 |
| 4,918,060 | 4/1990 | Kuncl et al. | 514/46 |

FOREIGN PATENT DOCUMENTS

| | | |
|---|---|---|
| 0351475 | 1/1990 | European Pat. Off. |
| 0358536 | 2/1990 | European Pat. Off. |

OTHER PUBLICATIONS

CA 103: 4864c, DiPadova et al., 1985.

Primary Examiner—Frederick E. Waddell
Assistant Examiner—Kimberly R. Jordan
Attorney, Agent, or Firm—T. Helen Payne; Louis J. Wille

[57] ABSTRACT

The present invention relates to a method of effecting immunosuppression in a patient in need thereof comprising administering to said patient an effective immunosuppressive amount of certain 5'-amine substituted adenosine analogs.

8 Claims, No Drawings

5'-AMINE SUBSTITUTED ADENOSINE ANALOGS AS IMMUNOSUPPRESSANTS

CROSS-REFERENCE TO RELATED APPLICATION

This is a continuation of application Ser. No. 07/840,658, filed Feb. 20, 1992; which is a continuation of application Ser. No. 07/571,042, filed Aug. 22, 1990, both now abandoned.

FIELD OF THE INVENTION

This invention relates to the method of use of certain 5'-amine substituted adenosine analogs which are useful as immunosuppressants.

BACKGROUND OF THE INVENTION

Immunity is concerned with the recognition and disposal of foreign antigenic material which is present in the body. Typically the antigens are in the form of particulate matter (i.e., cells, bacteria, etc.) or large protein or polysaccharide molecules which are recognized by the immune system as being "non-self", i.e., detectably different or foreign from the animals own constituents. Potential antigens can be a variety of substances, often proteins, which are most frequently located on the outer surfaces of cells. For example, potential antigens can be found on pollen grains, tissue grafts, animal parasites, viruses, and bacteria. Once the antigenic material is recognized as "non-self" by the immune system, natural (non-specific) and/or adaptive immune responses can be initiated and maintained by the action of specific immune cells, antibodies and the complement system. Under certain conditions, including in certain disease states, an animal's immune system will recognize its own constituents as "non-self" and initiate an immune response against "self" material.

An immune response can be carried out by the immune system by means of natural or adaptive mechanisms, each of which are composed of both cell-mediated and humoral elements. Natural mechanisms for immune response refer to those mechanisms involved in essentially non-specific immune reactions which involve the complement system and myeloid cells alone, such as macrophages, mast cells and polymorphonuclear leukocytes (PMN), in reacting to certain bacteria, viruses, tissue damage and other antigens. These natural mechanisms provide what is referred to as natural immunity. Adaptive mechanisms for immune response refer to those mechanisms which are mediated by lymphocytes (T and B cells) and antibodies which can respond selectively to thousands of different materials recognized as "non-self". These adaptative mechanisms provide what is referred to as adaptive immunity and lead to a specific memory and a permanently altered pattern of response in adaptation to the animal's own environment. Adaptive immunity can be provided by the lymphocytes and antibodies alone or, more commonly, can be provided by the interaction of lymphocytes and antibodies with the complement system and myeloid cells of the natural mechanisms of immunity. The antibodies provide the humoral element of the adaptive immune response and the T-cells provide cell-mediated element of the adaptive immune response.

Natural mechanisms of immune response involve phagocytosis macrophages and PMN whereby foreign material or antigen is engulfed and disposed of by these cells. In addition, macrophages can kill some foreign cells through its cytotoxic effects. The complement system which is also involved in natural immunity is made up of various peptides and enzymes which can attach to foreign material or antigen and thereby promote phagocytosis by macrophages and PMN, or enable cell lysis or inflammatory effects to take place.

Adaptive mechanisms of immune response involve the actions against specific antigens of antibody secreted by B-lymphocytes (or B-cells) as well as the actions of various T-lymphocytes (or T-cells) on a specific antigen, on B-cells, on other T-cells and on macrophages.

Antibodies, which are responsible for the humoral aspect of adaptive immunity, are serum globulins secreted by B-cells with a wide range of specificity for different antigens. Antibodies are secreted in response to the recognition of specific antigens and provide a variety of protective responses. Antibodies can bind to and neutralize bacterial toxins and can bind to the surface of viruses, bacteria, or other cells recognized as "non-self" and thus promote phagocytosis by PMN and macrophages. In addition, antibodies can activate the complement system which further augments the immune response against the specific antigen.

Lymphocytes are small cells found in the blood which circulate from the blood, through the tissues, and back to the blood via the lymph system. There are two major subpopulations of lymphocytes called B-cells and T-cells. B-cells and T-cells are both derived from the same lymphoid stem cell with the B-cells differentiating in the bone marrow and the T-cells differentiating in the thymus. The lymphocytes possess certain restricted receptors which permit each cell to respond to a specific antigen. This provides the basis for the specificity of the adaptive immune response. In addition, lymphocytes have a relatively long lifespan and have the ability to proliferate clonally upon receiving the proper signal. This property provides the basis for the memory aspect of the adaptive immune response.

B-cells are the lymphocytes responsible for the humoral aspect of adaptive immunity. In response to recognition of a specific foreign antigen, a B-cell will secrete a specific antibody which binds to that specific antigen. The antibody neutralizes the antigen, in the case of toxins, or promotes phagocytosis, in the case of other antigens. Antibodies also are involved in the activation of the complement system which further escalates the immune response toward the invading antigen.

T-cells are the lymphocytes responsible for the cell-mediated aspect of adaptive immunity. There are three major types of T-cells, i.e., the Cytotoxic T-cells, Helper T-cells and the Suppressor T-cells. The Cytotoxic T-cells detects and destroys cells infected with a specific virus antigen. Helper T-cells have a variety of regulatory functions. Helper T-cells, upon identification of a specific antigen, can promote or enhance an antibody response to the antigen by the appropriate B-cell and it can promote or enhance phagocytosis of the antigen by macrophages. Suppressor T-cells have the effect of suppressing an immune response directed toward a particular antigen.

The cell-mediated immune response is controlled and monitored by the T-cells through a variety of regulatory messenger compounds secreted by the myeloid cells and the lymphocyte cells. Through the secretion of these regulatory messenger compounds, the T-cells can regulate the proliferation and activation of other immune cells such as B-cells, macrophages, PMN and other T-cells. For example, upon binding a foreign antigen, a macrophage or other antigen presenting cell can secrete interleukin-1 (IL-1) which activates the Helper T-cells. T-cells in turn secrete certain lymphokines, including interleukin-2 (IL-2) and γ-interferon, each of which have a variety of regulatory effects in the cell-mediated immune response. Lymphokines are a large family of molecules produced by T-cells (and sometimes B-cells) including IL-2, which promotes the clonal proliferation of T-cells;

MAF or macrophage activation factor, which increases many macrophage functions including phagocytosis, intracellular killing and secretion of various cytotoxic factors;

NAF or neutrophil activation factor, which increases many functions of the PMN including phagocytosis;

MIF or macrophage migration factor, which by restricting the movement of macrophages, concentrates them in the vicinity of the T-cell;

γ-interferon, which is produced by the activated T-cell and is capable of producing a wide range of effects on many cells including inhibition of virus replication, induction of expression of class II histocompatibility molecules allowing these cells to become active in antigen binding and presentation, activation of macrophages, inhibition of cell growth, induction of differentiation of a number of myeloid cell lines.

Activated macrophages and PMNs, which provide an enhanced immune response as part of the cell-mediated adaptive immunity, are characterized as having increased production of reactive oxygen intermediates. This increased production of reactive oxygen intermediates, or respiratory burst, is known as "priming". Certain lymphokines, such as γ-interferon, trigger this respiratory burst of reactive oxygen intermediates in macrophages and PMNs. Thus, lymphokines, such as γ-interferon, which are secreted by the T-cells provide an activation of these macrophages and PMNs which results in an enhanced cell-mediated immune response.

The immune response can provide an immediate or a delayed type of response. Delayed-type hypersensitivity is an inflammatory reaction which occurs in immune reactive patients within 24-48 hours after challenge with antigen and is the result primarily of a cell-mediated immune response. In contrast, immediate-type hypersensitivity, such as that seen in anaphylactic or Arthus reactions, is an inflammatory reaction which occurs in immune reactive patients within minutes to a few hours after challenge with antigen and is the result primarily of humoral or antibody-mediated immune response.

The ability of the immune system, and in particular the cell-mediated immune system, to discriminate between "self" and "non-self" antigens is vital to the functioning of the immune system as a specific defense against invading microorganisms. "Non-self" antigens are those antigens on substances in the body which are detectably different or foreign from the animals own constituents and "self" antigens are those antigens which are not detectably different or foreign from the animals own constituents. Although the immune response is a major defense against foreign substances which can cause disease, it cannot distinguish between helpful and harmful foreign substances and destroys both.

There are certain situations, such as with an allogeneic transplant or in "graft versus host" disease, where it would be extremely useful to suppress the immune response in order to prevent the rejection of helpful foreign tissue or organs. Allogeneic tissues and organs are tissues and organs from a genetically different member of the same species. "Graft versus host" disease occurs where the transplanted tissue, for example in a bone marrow transplant, contains allogeneic T-cells of the donor which cause an immune response against the recipient's own tissues. Although both humoral and cell-mediated immune responses play a role in the rejection of allogeneic tissues and organs, the primary mechanism involved is the cell-mediated immune response. Suppression of the immune response, and in particular, suppression of cell-mediated immune response, would thus be useful in preventing such rejection of allograft tissues and organs. For example, cyclosporin A is currently used as an immunosuppressive agent in the treatment of patients receiving allogeneic transplants and in "graft versus host" disease.

There are times when the individual's immunological response causes more damage or discomfort than the invading microbes or foreign material, as in the case of allergic reactions. Suppression of the immune response in these cases would be desirable.

Occasionally, the immunological mechanisms become sensitized to some part of the individual's own body causing interference with or even destruction of that part. The ability to distinguish between "self" and "not self" is impaired and the body begins to destroy itself. This can result in an autoimmune diseases such as rheumatoid arthritis, insulin-dependent diabetes mellitus (which involves the autoimmune destruction of the β-cells of the islets of Langerhans which are responsible for the secretion of insulin), certain hemolytic anemias, rheumatic fever, thyroiditis, ulceractive colitis, myestheniagravis, glomerulonephritis, allergic encephalomyelitis, continuing nerve and liver destruction which sometimes follows viral hepatitis, multiple sclerosis and systemic lupus erythematosus. Some forms of autoimmunity come about as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-react with, the individual's own tissue. Rheumatic fever is an example of this type of disease in which the antigen of the streptococcal bacterium which causes rheumatic fever is cross-reactive with parts of the human heart. The antibodies cannot differentiate between the bacterial antigens and the heart muscle antigens and cells with either of those antigens can be destroyed. Suppression of the immune system in these autoimmune diseases would be useful in minimizing or eliminating the effects of the disease. Certain of these autoimmune diseases, for example, insulin-dependent diabetes mellitus, multiple sclerosis and rheumatoid arthritis, are characterized as being the result of a cell-mediated autoimmune response and appear to be due to the action of T-cells [See Sinha et al. *Science* 248, 1380 (1990)].

Suppression of the immune response would thus be useful in the treatment of patients suffering from autoimmune diseases. More particularly, suppression of cell-mediated immune response would thus be useful in the treatment of patients suffering from autoimmune diseases due to the action of T-cells such as insulin-dependent diabetes mellitus, multiple sclerosis and rheumatoid arthritis.

SUMMARY OF THE INVENTION

The present invention provides a method of effecting immunosuppression in a patient in need thereof comprising administering to said patient an effective immunosuppressive amount of a compound of the formula (1) wherein

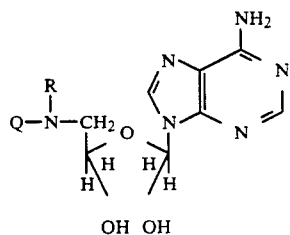

R represents H, methyl or ethyl and
Q represents a radical of formulae Ia to If depicted as follows:

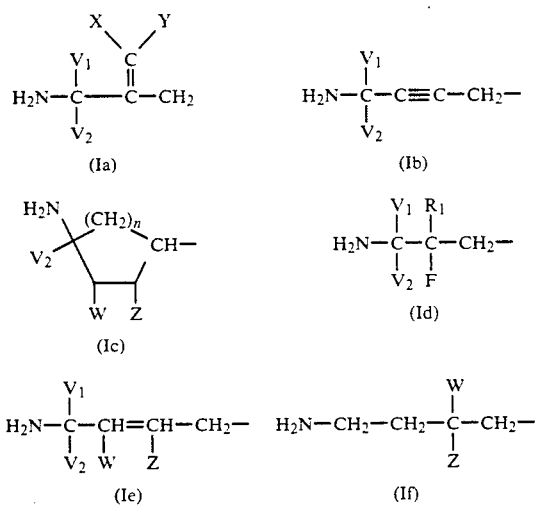

wherein
$R_1$ is H or F,
n is an integer 1 or 2,
$V_1$ is H or methyl,
$V_2$ is H or COOH, and
W, X, Y and Z are each independently H, F, Cl or Br;
or a pharmaceutically acceptable salt thereof.

More particularly, the present invention provides a method of suppressing cell-mediated immunity in a patient in need thereof comprising administering to said patient an effective immunosuppressive amount of a compound of formula (1).

DETAILED DESCRIPTION OF THE INVENTION

As used herein, the term "H" refers to a hydrogen atom, "F" refers to a fluorine atom, "Cl" refers to a chlorine atom, "Br" refers to a bromine atom and "COOH" refers to a carboxy group.

Illustrative examples of pharmaceutically acceptable salts of the compounds of this invention are those formed with inorganic acids preferably with hydrochloric, hydrobromic, sulfuric or phosphoric acids and with organic acids such as methane sulfonate, salicylic, maleic, malonic, tartaric, citric and ascorbic acids. These salts may be prepared by standard techniques and procedures well known in the art.

In essence, the preparation of the compounds of formula I may be effected by techniques and chemical processes analogously known in the art; the choice of the specific route being dependent upon the usual factors in pharmaceutical research institutions such as availability and cost of starting materials, time and difficulties in separation and purification of intermediates and final compounds and such other factors well known and generally appreciated by those of ordinary skill in the art.

In general, the compounds of formula (1) may be prepared according to the reaction sequence described in Reaction Scheme A.

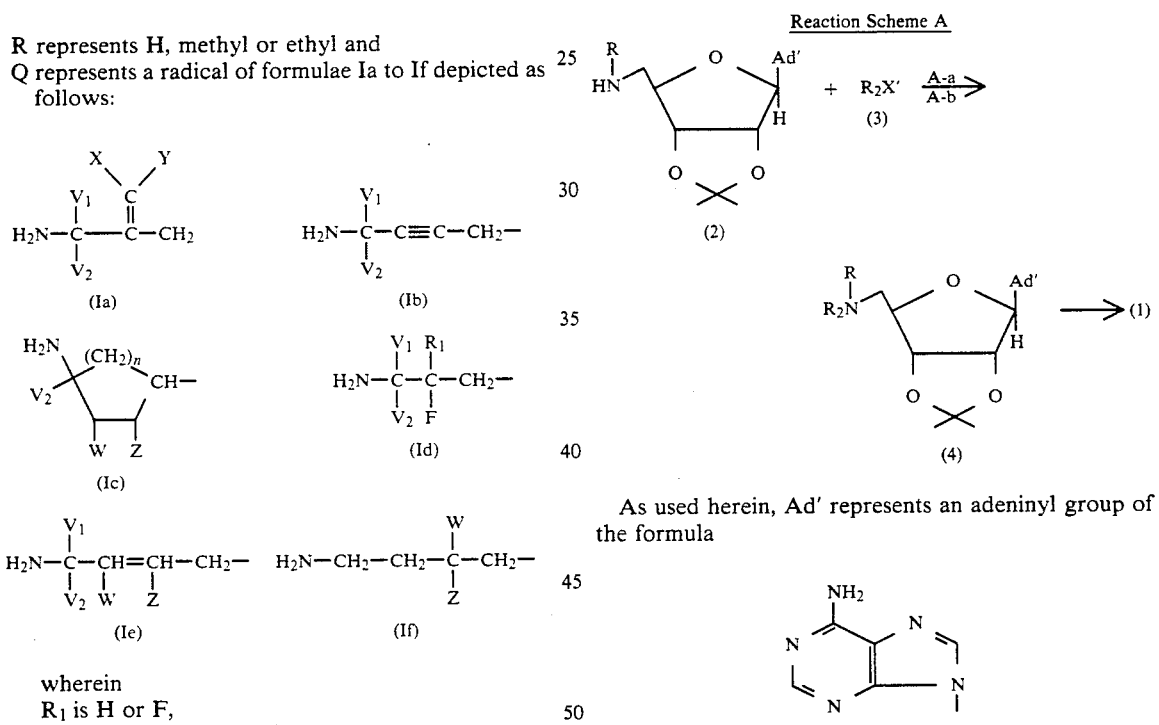

As used herein, Ad' represents an adeninyl group of the formula

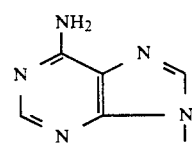

and $R_2X'$ is a reactant of the following formulae (3a to 3f):

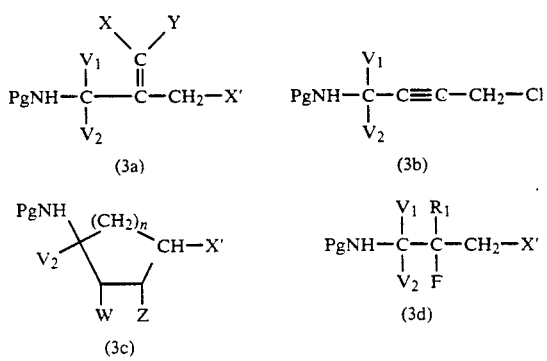

-continued

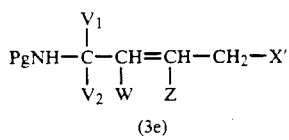

(3e)

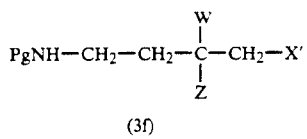

(3f)

As used herein, Pg represents an N-protecting group, preferably t-butoxycarbonyl (Boc) or phthalimido (Pht) (in which case, of course, the H of the PgNH moiety is not present). X' represents a OTF (triflate) or chloro, bromo or iodo group. R, $R_1$, $V_1$, $V_2$, n, W, X, Y and Z are as defined in formula (1). $R_2$, of course, represents the moieties of 3a to 3f attached to the X' moiety. Where $V_2$ is COOH, $V_2$ may be a reaction-protected derivative of the COOH function such as a t-butoxy derivative. In addition, the 2'- and 3'-hydroxy groups of the ribofuranosyl moiety of reactant 2 are blocked with an isopropylidene protecting group.

In effecting the condensation of reactants 2 and 3 when X' represents a halide, conditions A-a are utilized wherein equimolar quantities of the reactants are reacted together in the presence of a base (preferably potassium carbonate), in a basic solvent (preferably acetonitrile), at temperatures of about 30° C. to 80° C. When X' is a triflate, conditions A-b are utilized wherein the reactants are heated together at about 30° C. to 80° C. in the presence of a base (preferably triethylamine), in a basic solvent (preferably dimethylformamide).

Removal of the N-protecting groups is readily effected by standard techniques. When the protecting group is t-butoxycarbonyl, the protecting group may be removed, for example, by treatment with 1N sulfuric acid at room temperature for 24-48 hours followed by treatment with an alcohol (preferably ethanol) at about 0° C. When the protecting group is phthalimido, removal may be effected using an ethanolic solution of a hydrazine (using classical techniques). The phthalimido protecting group is utilized when $R_2$ contains a fluoro atom. Removal of the isopropylidene protecting group of the ribofuranosyl moiety is easily effected by hydrolysis at room temperatures, (preferably using 1N sulfuric acid), generally simultaneously with the N-protecting groups.

Isolation and purification of the intermediate and final products of reaction Scheme A is effected by standard techniques, e.g., recrystallization, HPLC, flash chromatography (on silica gel) and the like.

The preparation of the intermediates required for the condensation of reaction Scheme A, i.e., those intermediates defined for $R_2X'$, may also be effected by the use of analogously known procedures such as those outlined in the below described generic processes which are illustrated in the below particularized examples.

In those instances wherein $R_2X'$ represents subgeneric group 3e, the reaction proceeds under A-a conditions wherein X' is preferably chloro and the N-protecting group is preferably Boc. The appropriate $V_1$, $V_2$, W, Z-substituted-N-protected-4-chloro-2-butene-1-amine may conveniently be prepared by the following Reaction Scheme B wherein the protecting groups (Pht and Boc) and $V_1$, $V_2$, W and Z are as previously defined and (THP) is tetrahydropyran.

Reaction Scheme B

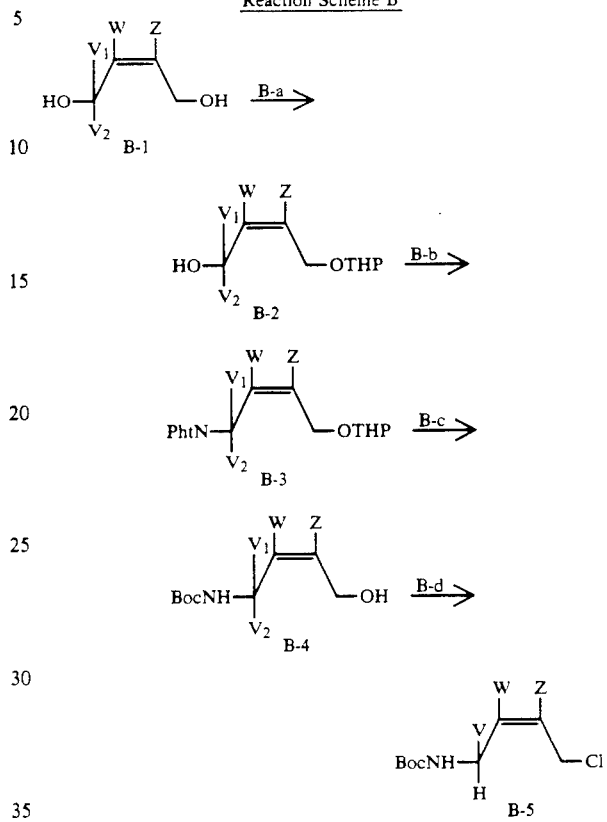

In step B-a, the cis-diol B-1 is reacted with dihydropyran in the presence of catalytic quantities of pyridinium-p-toluene sulfonate at about 0° C. in an anhydrous solvent (or mixture) (e.g., $CH_2Cl_2$:THF; 2:1) for about 24-48 hours.

In step B-b, B-2 is converted to B-3 by a Mitsunobu-type intermolecular dehydration reaction. B-2 is treated with diethylazodicarboxylate (DEAD) and triphenylphosphine under mild neutral conditions under an inert atmosphere (nitrogen) at about 0° C. in an anhydrous solvent (e.g., THF) in the presence of phthalimide with the reaction continuing at room temperature for about 12 hours.

In step B-c, B-3 is treated with hydrazine hydrate in ethanol at reflux for about 12 hours, to remove the phthalimido and THP protecting groups. The resulting free amine is re-protected with di-t-butyldicarbonate by refluxing in dichloromethane.

In step B-d, the alcohols (B-4) are converted to their chlorides by reaction with mesylchloride under basic conditions (TEA) in an anhydrous solvent, preferably dichloromethane. These cis products of formula (3e), after purification, generally using flash chromatographic techniques on silica gel, are ready for condensation with the reactants of formula (2), according to the techniques described for Reaction Scheme A.

In those instances wherein it is desired to prepare the trans-configuration of compounds of 3-e, it is preferred to utilize a W, Z, $V_1$, $V_2$-substituted N-protected trans-1-bromo-4-amino-2-butene. The appropriate reactant is readily prepared by reacting a W, Z, $V_1$, $V_2$-substituted trans-1-bromo-4-amino-2-butene with potassium phthalimide in anhydrous DMF at about 50° C. for 24 hours according to standard procedures well known in the art.

The necessary $R_2X'$ reactants of the class 3-c are readily prepared from the appropriate W, Z, $V_2$-substituted α,α-dichloroxylene wherein the compound is subjected to a displacement reaction with potassium phthalimide to form an α-phthalimido-α'-chloroxylene by heating the reactants at about 50° C. for about 24 hours in anhydrous DMF and the so-formed compound is purified by the usual techniques of flash chromatography from silica gel.

Starting from the appropriately $V_1$, $V_2$, X, Y-substituted 3-chloro-2-chloromethyl-1-propene the desired $R_2X'$ reactants of class 3-a may similarly be prepared by the foregoing described displacement reaction with potassium phthalimide by heating the reactants at about 50° C. for about 24 hours in anhydrous dimethylfluoromethane followed by purification with the usual techniques, e.g., flash chromatography. In those instances wherein the particular $V_1$, $V_2$, X, Y-substituted reactant is not a known compound, such compounds may be prepared by techniques and procedures well understood and known in the art.

In addition to the specific examples described below, chemistry for the preparation of cis-5'-(4-amino-4-carboxy-2-butenyl)methyladenosine may be analogously derived from Tolman and Sedmera's article (Tetrahedron Letters, Vol. 29, No. 47, pp. 6183–6184, 1988) "Unsaturated Amino Acids: Synthesis of Trans-3,4-Didehydro Analogues of L-Ornithine and L-Arginine". The application of this chemistry is schematically represented by the following Reaction Scheme C wherein the term "Ac" refers to a acyl group.

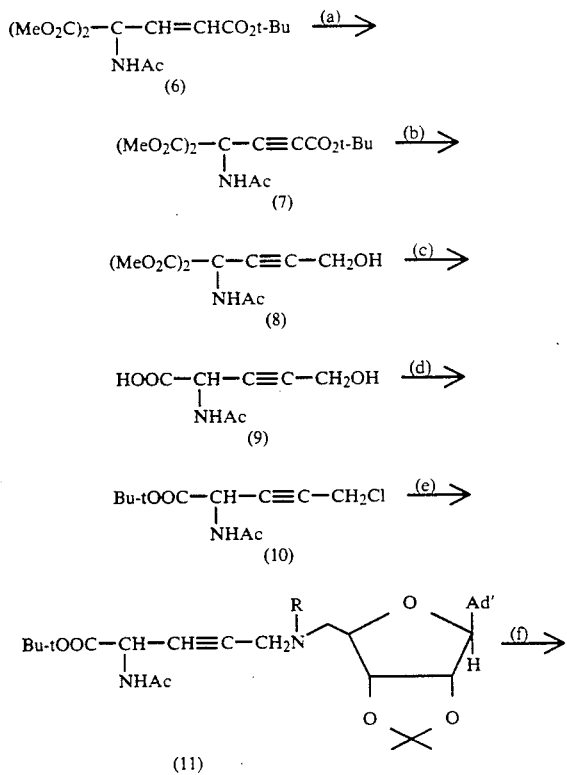

Reaction Scheme C

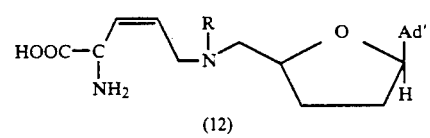

In effecting the foregoing reaction scheme step (a) involves the dibromination of (6) by reaction with bromine, said reaction being placed in a suitable solvent (e.g., $CCl_4$) at room temperature. The resulting dibromo analog is debrominated by reaction with potassium t-butoxide in tetrahydrofuran or with an amine such as DBU. The so-obtained compound (7) is sequentially treated with (1) trifluoroacetic acid at 25° C. for 20 minutes, (2) treated with thionyl chloride at 25° C. for 3 hours, and (3) treated with DiBal in tetrahydrofuran at −30° C. for 1 hour to produce compound (8). Step (c) involves the sequential treatment of (8) with a base (e.g., $NaOH/H_2O$ in tetrahydrofuran for 20 minutes, followed by treatment with diluted HCl at 50° C. to produce compound (9). This compound is treated with isobutylene, in the presence of catalytic amounts of sulfuric acid and the resulting alcohol is converted to its corresponding chloride by treatment with mesyl chloride to produce compound (10). This compound is then subjected to reaction with the adenosine derivatives of formula (2) according to the procedure of Reaction Scheme A (wherein compound (10) corresponds to $R_2X'$ with X' being chloro) to produce a compound analogously corresponding to compound (4) [i.e., compound (11)].

The resulting triple-bond-containing compound is partially reduced using hydrogenation in the presence of a Lindlar catalyst ($H_2/PdSO_4$) and the resulting butene is treated with sulfuric acid (to remove the t-butoxide and isopropylidene protecting groups). The final step is to subject the so-produced penultimate compound to acylase I (Merck) at a pH of 7.2 at 37° C. to remove the N-protecting acyl moiety to produce a desired compound (12), e.g., cis-5'-deoxy-5'-(4-amino-4-carboxy-2-butene)methylaminoadenosine.

The following examples illustrate the preparation of the necessary intermediates and final products of this invention.

EXAMPLE 1

Preparation of Cis-5'-Deoxy-5'(4-Amino-2-Butenyl)Methylaminoadenosine

Step A: Cis-4-Tetrahydropyranyloxy-2-Butene-1-Ol

Dihydropyrane (9.1 ml, 100 mmol) was added dropwise to a cooled (0° C.) solution of 2-butene-1,4-diol (8.8 g, 10 mmol) and pyridinium paratoluenesulfonate (0.25 g, 10 mmol) in anhydrous dichloromethane:tetrahydrofuran (2:1). The mixture was stirred two days at 0° C. then concentrated in vacuo. The residue was purified by flash chromatography on silica gel (ethyl acetate:hexane 3:7) to give 8.3 g of the title compound (49%).

Step B: Cis-1-Phthalimido-4-Tetrahydropyranyloxy-2-Butene

Under a nitrogen atmosphere diethylazodicarboxylate (1.6 ml, 10 mmol) was added to a cooled (0° C.) solution of cis-4-tetrahydropyranyloxy-2-butene-1-ol (1.7 g, 10 mmol), triphenyl phosphine (2.2 g, 10 mmol) and phthalimide (1.47 g, 10 mmol) in anhydrous tetrahydrofuran (50 ml). When the addition was completed (5 min) the reaction mixture was allowed to warm at room temperature and was stirred 12 h. Then the mixture was concentrated in vacuo, diluted with ethyl acetate (200 ml) and washed with brine (150 ml). After usual work-up (the aqueous phase was extracted three times with 100 ml portions of ethyl acetate), the organic phase was dried over magnesium sulfate, filtered and concentrated in vacuo) the product was purified by flash chromatography on silica gel (ethyl acetate:hexane; 2:8) to give 1.9 g of the title compound (64%).

Step C: Cis-Tertiobutoxycarbonyl-4-Hydroxy-2-Butenyl-1-Amine

A solution of cis-1-phthalimido-4-tetrahydropyranyloxy-2-butene (1.9 g, 6.3 mmol) and hydrazine hydrate (0.35 ml, 6.9 mmol) in ethanol (20 ml) was heated under reflux 12 hours. Then the mixture was concentrated in vacuo, diluted with 1N hydrochloric acid (20 ml) and heated under reflux for two hours. Then the phthalylhydrazide was filtered off and the filtrate was concentrated in vacuo. The residue was taken in dichloromethane (100 ml) neutralized with triethylamine (pH 8.9) and a solution of ditertiobutyldicarbonate (1.65 g, 7.5 mmol) in dichloromethane (5 ml) was added. The mixture was heated under reflux overnight and, after usual work-up, the product was obtained by flash chromatography on silica gel (ethyl acetate: hexane; 25:75) (0.8 g, 74%).

Step D: Cis-N-Tertiobutoxycarbonyl-4-Chloro-2-Butenyl-1-Amine

Mesyl chloride (0.6 ml, 7.6 mmol) was added to a cooled (0° C.) solution of cis-tertiobutoxycarbonyl-4-hydroxy-2-butenyl-1-amine (1.3 g, 7 mmol) and triethylamine (1.1 ml, 7.6 mmol) in anhydrous dichloromethane (30 ml). The mixture was stirred overnight and, after usual work-up, the title product was purified by flash chromatography on silica gel (ethyl acetate: hexane; 2:8) (0.8 g, 57%).

Step E: Cis-5'-Deoxy-5'(N-Tertiobutoxycarbonyl-4-Amino-2-Butenyl)Methyl-Amino-2',3'-Isopropylideneadenosine A solution of cis-N-tertiobutoxycarbonyl-4-chloro-2-butenyl-1-amine (0.6 g, 3 mmol), 5'-deoxy-5'-methylamino-2',3'-isopropylideneadenosine (0.97 g, 3 mmol), potassium carbonate (0.42 g, 3 mmol) and sodium iodide (0.05 g, 0.3 mmol) in acetonitrile (20 ml) was heated under reflux overnight. Then the mixture was diluted with ethyl acetate, washed with brine and dried over magnesium sulphate. Then the product was purified by flash chromatography on silica gel (diethyl amine:chloroform; 2:98) (1.1 g, 55%).

Step F: Cis-5'-Deoxy-5'(4-Amino-2-Butenyl)Methylaminoadenosine

A solution of cis-5'-deoxy-5'[(N-tertiobutoxycarbonyl-4-amino-2-butenyl)methyl-amino]-2',3'-isopropylideneadenosine (0.9 g, 1.8 mmol) in 1N sulphuric acid (5 ml) was left two days at room temperature. Then the mixture was diluted with ethanol (200 ml) and cooled (0° C.) overnight. The precipitate was filtered off, dissolved in the minimum amount of water and then re-precipitated with ethanol (200 ml). This procedure was repeated twice to give the title compound (0.5 g), mp: 260° C. decomposed.

EXAMPLE II

Preparation of Trans-5'-Deoxy-5'-(4-Amino-2-Butenyl)Methylaminoadenosine

Step A: Trans-1-Bromo-4-Phthalimido-2-Butene

A mixture of trans-1,4-dibromo-2-butene (6.4 g, 30 mmol) and potassium phthalimide (5.6 g, 30 mmol) in anhydrous dimethyl formamide (200 ml) was heated at 50° C. for 24 h. Then the reaction mixture was concentrated in vacuo, dissolved in ethyl acetate, washed with brine and the pure title product was obtained by flash chromatography on silica gel (ethyl acetate: hexane; 15:85) (3.2 g, 40%).

Step B: Trans-5'-Deoxy-5'-(4-Phthalimido-2-Butenyl)Methylamino-2',3'-Isopropylideneadenosine A mixture of trans-1-bromo-4-phthalimido-2-butene (2 g, 7.5 mmol), potassium carbonate (1.6 g, 11.5 mmol) and 5'-deoxy-5'-methylamino-2',3'-isopropylideneadenosine (2.4 g, 7.5 mmol) in anhydrous acetonitrile (100 ml) was heated under reflux overnight. Then the mixture was concentrated in vacuo, dissolved in dichloromethane, filtered and purified by flash chromatography on silica gel (chloroform: diethylamine; 98:2) to afford the title compound (1.25 g, 33%).

Step C: Trans-5'-Deoxy-5'-(4-Tertiobutoxycarbonylamino-3-Butenyl)Methylamino-2',3'-Isopropylideneadenosine A mixture of trans-5'-deoxy-5'-(4-phthalimido-2-butenyl)methylamino-2',3'-isopropylideneadenosine (1 g, 2 mmol) and hydrazine hydrate (0.1 ml, 2 mmol) in absolute ethanol was heated under reflux overnight. Then the mixture was concentrated in vacuo, dissolved in water (30 ml) and the pH was adjusted to 4 with glacial acetic acid and cooled to 0° C. Then the mixture was filtered off and the filtrate neutralized with triethylamine to pH 9 and concentrated in vacuo. Then the residue was dissolved in dichloromethane, and ditertiobutyldicarbonate (0.45 g, 2 mmol) was added. The mixture was heated under reflux overnight and, after usual work-up, the product was purified by flash chromatography on silica gel (diethylamine:dichloromethane; 2:98) to give the title compound (0.5 g, 51%).

Step D: Trans-5'-Deoxy-5'-(4-Amino-2-Butenyl)Methylaminoadenosine

A suspension of trans-5'-deoxy-5'-(4-tertiobutoxycarbonylamino-2-butenyl)methylamino-2',3'-isopropylideneadenosine (0.4 g, 0.96 mmol) in 1N sulphuric acid (3 ml) was stirred 2 days at room temperature. Then the mixture was diluted with absolute ethanol (100 ml) and cooled at 0° C. overnight. The product was filtered off, dissolved in the minimum amount of water and precipitated with ethanol (100 ml). This procedure was repeated twice to afford the title compound (0.16 g). mp: 250°–260° C. decomposed.

EXAMPLE III

Preparation of
5'-Deoxy-5'-(4-Amino-2-Butynyl)Methylaminoadenosine

Step A: 1-Chloro-4-Phthalimido-2-Butnye

A mixture of 1,3-dichloro-2-butyne (4.9 ml, 50 mmol) and potassium phthalimide (5.6 g, 30 mmol) was heated at 50° C. during 24 h. Then the mixture was concentrated in vacuo, diluted with ethyl acetate and, after usual work-up, the product was purified by flash chromatography on silica gel to give 4.3 g of the title compound (62%).

Step B:
5'-Deoxy-5'-(4-Phthalimido-2-Butynyl)Methylamino-2',3'-Isopropylideneadenosine A mixture of 1-chloro-4-phthalimido-2-butyne (1.4 g, 6 mmol), 5'-deoxy-5'-methylamino-2',3'-isopropylideneadenosine (1.6 g, 5 mmol) and sodium iodide (0.075 g, 0.5 mmol) in anhydrous acetonitrile (100 ml) was heated under reflux overnight. Then the mixture was concentrated, diluted with dichloromethane, filtered and purified by flash chromatography on silica gel (diethylamine:chloroform; 2:98) to give the title compound (1.6 g, 64%).

Step C:
5'-Deoxy-5'-(4-Tertiobutoxycarbonylamino-2-Butynyl)Methylamino-2',3'-Isopropylideneadenosine A mixture of 5'-deoxy-5'-(4-phthalimido-2-butynyl)-methylamino-2',3'-isopropylideneadenosine (1 g, 1.9 mmol) and methyl hydrazine (0.5 ml, 10 mmol) in absolute ethanol (3 ml) was heated under reflux overnight. Then the mixture was concentrated in vacuo, dissolved in a mixture of tetrahydrofuran:water (1:1, 200 ml), and a solution of ditertiobutyl dicarbonate (0.5 g, 2.5 mmol) in tetrahydrofuran (10 ml) was added. The pH of the mixture was adjusted to 9 with triethylamine and then the mixture was heated under reflux for 24 h. Then the reaction mixture was concentrated in vacuo, diluted with ethyl acetate and, after usual work-up, the product was obtained by flash chromatography on silica gel (diethylamine:chloroform; 2:98) (0.5 g, 56%).

Step D:
5'-Deoxy-5'-(4-Amino-2-Butynyl)Methylaminoadenosine

A suspension of 5'-deoxy-5'-(4-tertiobutoxycarbonylamino-2-butynyl)methylamino-2',3'-isopropylideneadenosine (0.4 g, 0.82 mmol) in 1N sulphuric acid (25 ml) was stirred 2 days at room temperature. Then the mixture was diluted with ethanol (100 ml;) and stirred at 0° C. overnight. The product was filtered off, dissolved in the minimum amount of water and diluted with ethanol (100 ml). This procedure was repeated twice to afford pure 5'-deoxy-5'-(4-amino-2-butynyl)methylaminoadenosine as white crystals (0.2 g). mp: 230°-240° C. decomposed. This compound, of course, can be reduced to form the corresponding cis double-bonded compound.

EXAMPLE IV

Preparation of 5'-Deoxy-5'-(Ortho-Aminomethyl Benzyl)Methylaminoadenosine

Step A: α-Phthalimido-α'-Chloroxylene

A mixture of α,α'-dichloroxylene (8.75 g, 50 mmol) and potassium phthalimide (5.6 g, 30 mmol) was heated to 50° C. for 24 h. Then the reaction mixture was concentrated in vacuo, dissolved in ethyl acetate and, after usual work-up, the desired compound was obtained by flash chromatography on silica gel (ethyl acetate:hexane; 15:85) (6 g, 65%).

Step B:
5'-Deoxy-5'-(Ortho-Phthalimido-Methylbenzyl)Methylamino-2',3-Isopropylideneadenosine A mixture of α-phthalimido-α'-chloroxylene (1.6 g, 5.5 mmol), potassium carbonate (0.7 g, 5 mmol) sodium iodide (0.07 g, 0.5 mmol) and 5'-deoxy-5'-methylamino-2',3'-isopropylideneadenosine (1.5 g, 4.7 mmol) in anhydrous acetonitrile was heated under reflux overnight. Then the mixture was concentrated in vacuo, dissolved in dichloromethane, filtered and then purified by flash chromatography on silica gel (chloroform: diethylamine 98:2) to give the title compound (1.8 g, 67%).

Step C:
5'-Deoxy-5'-(Ortho-Tertiobutoxycarbonylaminomethylbenzyl)Methylamino-2',3'-Isopropylideneadenosine A mixture of 5'-deoxy-5'-(ortho-phthalimido-methylbenzyl)methylamino-2',3'-isopropylideneadenosine (1.3 g, 2.3 mmol) and hydrazine hydrate (0.12 ml, 2.3 mmol) in absolute ethanol (100 ml) was heated under reflux overnight. Then the mixture was concentrated in vacuo, diluted in water (30 ml), and glacial acetic acid was added to adjust at pH 4 and left at 0° C. Then the mixture was filtered off and the filtrate was neutralized with triethylamine to adjust the pH of the reaction mixture around 9. Then the mixture was concentrated in vacuo, diluted with dichloromethane, and ditertiobutyldicarbonate (0.5 g, 2.3 mmol) was added. Then the mixture was heated under reflux overnight and, after usual work-up, the title compound (0.8 g, 67%) was isolated by flash chromatography on silica gel (chloroform: diethylamine; 98:2).

Step D:
5'-Deoxy-5'-(Ortho-Aminomethylbenzyl)Methylaminoadenosine

A suspension of 5'-deoxy-5'-(ortho-tertiobutoxycarbonylaminomethylbenzyl)methylamino-2',3'-isopropylideneadenosine (0.45 g, 0.83 mmol) in 1N sulphuric acid (25 ml) was stirred two days at room temperature. Then the mixture was diluted with ethanol (100 ml) and stored at 0° C. overnight. The precipitate was filtered off, dissolved in the minimum amount of water and reprecipitated with ethanol (100 ml). This procedure was repeated twice to give the title compound (0.4 g). mp: 230°-240° C. decomposed.

EXAMPLE V

5'-Deoxy-5'-(3-Amino-2-Methylenepropyl)Methylaminoadenosine

Step A: 1-Phthalimido-3-Chloro-2-Methylenepropane

A mixture of 3-chloro-2-chloromethyl-1-propene (6.55 g, 50 mmol) and potassium phthalimide (5.6 g, 30 mmol) in anhydrous dimethylformamide (200 ml) was heated two days at 50° C. Then the mixture was concentrated in vacuo and, after usual work-up, the product was purified by flash chromatography on silica gel (ethyl acetate:hexane; 15:85) (4.2 g, 78%).

Step B:
5'-Deoxy-5'-(3-Phthalimido-2-Methylenepropyl)Methylamino-2',3'-Isopropylideneadenosine A mixture of 1-phthalimido-3-chloro-2-methylenepropane (0.87 g, 5 mmol), potassium carbonate (0.7 g, 5 mmol), sodium iodide (0.08 g, 0.5 mmol) and 5'-deoxy-5'-methylamino-2',3'-isopropylideneadenosine (1.6 g, 5 mmol) in anhydrous acetonitrile (100 ml) was heated two days under reflux. Then the mixture was concentrated in vacuo, diluted with dichloromethane, filtered and the product was purified by flash chromatography on silica gel (diethylamine: chloroform; 2:98) to give 2.85 g (78%) of the title compound.

Step C:
5'-Deoxy-5'-(3-Tertiobutoxycarbonylamino-2-Methylenepropyl)Methylamino-2',3'-Isopropylideneadenosine A mixture of 5'-deoxy-5'-(3-phthalimido-2-methylenepropyl)methylamino-2',3'-isopropylideneadenosine (2.3 g, 4.4 mmol), methyl hydrazine (1.5 ml, 30 mmol) in absolute ethanol (5 ml) was heated two days under reflux. Then the mixture was concentrated in vacuo, dissolved in chloroform (5 ml), the pH was adjusted around 9 with triethylamine and then a solution of ditertiobutyl dicarbonate (8.8 g, 4.4 mmol) in chloroform (5 ml) was added. The resulting mixture was heated overnight under reflux and, after usual work-up, the product was purified by flash chromatography on silica gel (diethylamine: chloroform; 2:98) to give 1.25 g (64%) of the title compound.

Step D:
5'-Deoxy-5'-(3-Amino-2-Methylenepropyl)Methylaminoadenosine

A suspension of 5'-deoxy-5'-(3-tertiobutoxycarbonylamino-2-methylenepropyl)methylamino-2',3'-isopropylideneadenosine (0.65 g, 1.3 mmol) in 1N sulphuric acid (4 ml) was stirred two days at room temperature. Then the mixture was diluted with absolute ethanol (150 ml) and left at 0° C. overnight. The precipitate was filtered off, dissolved in a minimum amount of water and diluted with absolute ethanol (150 ml). This procedure was repeated twice to afford the title compound as white crystals (0.55 g, mp: 230°–240° C. decomposed).

EXAMPLE VI

Preparation of
5'-Deoxy-5'-(4-Amino-2,2-Difluorobutyl)Methylaminoadenosine

Step A:
4-Phthalimido-2,2-Difluorobutyl-Trifluoromethanesulfonate

Triflic anhydride (1.1 ml, 6.6 mmol) was added to a cooled (0° C.) solution of 4-phthalimido-2,2-difluoro-1-butanol (1.53 g, 6 mmol), pyridine (0.53 ml, 6.6 mmol) in anhydrous dichloromethane (50 ml). The mixture was stirred 1 h at 0° C. and, after usual work-up, the product was purified by flash chromatography on silica gel (ethyl acetate:hexane; 20:80) to give 1.8 g (78%) of the title compound.

Step B:
5'-Deoxy-5'-(4-Phthalimido-2,2-Difluorobutyl)Methylamino-2',3'-Isopropylideneadenosine A mixture of 4-phthalimido-2,2-difluorobutyl-trifluoromethanesulfonate (1.8 g, 4.6 mmol), 5'-deoxy-5'-methylamino-2',3'-isopropylideneadenosine (1.3 g, 4.3 mmol) and triethylamine (0.6 ml, 4.3 mmol) in anhydrous dimethylformamide was heated two days at 50° C. Then the mixture was concentrated in vacuo and the product was purified by flash chromatography on silica gel (diethylamine: chloroform; 2:98) (1.7 g, 70%).

Step C:
5'-Deoxy-5'-(4-Tertiobutoxycarbonylamino-2,2-Difluorobutyl)Methylamino-2',3'-Isopropylideneadenosine A mixture of 5'-deoxy-5'-(4-phthalimido-2,2-difluorobutyl)methylamino-2',3'-isopropylideneadenosine (1.5 g, 2.7 mmol) and hydrazine hydrate (0.135 g, 2.7 mmol) in ethanol (20 ml) was heated under reflux overnight. Then the mixture was concentrated in vacuo, diluted with water, and glacial acetic acid was added until the pH was adjusted to 4. The mixture was left at 0° C. and then filtered off. The filtrate was neutralized to pH 9 with triethylamine, concentrated in vacuo, diluted with dichloromethane and then ditertiobutyldicarbonate (0.6 g, 2.7 mmol) was added. The mixture was heated under reflux overnight and, after usual work-up, the product was purified by flash chromatography on silica gel (diethylamine: chloroform; 2:98) to give 1.1 g (75%) of the title compound.

Step D:
5'-Deoxy-5'-(4-Amino-2,2-Difluorobutyl)Methylaminoadenosine

A suspension of 5'-deoxy-5'-(4-tertiobutoxycarbonylamino-2,2-difluorobutyl)methylamino-2',3'-isopropylideneadenosine in 1N sulphuric acid (4.5 ml) was stirred two days at room temperature. Then the mixture was diluted with ethanol (100 ml) and left overnight at 0° C. The precipitate was filtered off, dissolved in a minimum amount of water and precipitated with ethanol (150 ml). This procedure was repeated twice to afford the title compound (0.5 g, 60%) as white crystals (mp: 240° C. decomposed).

EXAMPLE VII

Preparation of
Cis-5'-Deoxy-5'-(4-Amino-2Fluoro-2-Butenyl)Methylaminoadenosine

Step A:
Cis-4-Phthalimido-2-Fluoro-1-Tetrahydropyranyl-2-Butene

A mixture of cis-4-chloro-2-fluoro-1-tetrahydropyranyl-2-butene (6.3 g, 30 mmol) and potassium phthalimide (5.6 g, 30 mmol) in anhydrous dimethyl formamide (200 ml) was heated at 50° C. for 24 h. Then the reaction mixture was concentrated in vacuo, dissolved in ethyl acetate, washed with brine and the pure title compound cis-4-phthalimido-2-fluoro-2-tetrahydropyranyl-2-butene (6 g, 70%) was obtained by flash chromatography on silica gel (ethyl acetate:hexane; 2:8).

Step B:
Cis-N-Tertiobutoxycarbonyl-2-Fluoro-4-Hydroxy-2-Butenyl-1-Amine

A solution of cis-4-phthalimido-2-fluoro-2-tetrahydropyranyl-2-butene (5.7 g, 20 mmol) and hydrazine hydrate (1.1 ml, 22 mmol) in ethanol (30 ml) was heated under reflux for 12 h. Then the mixture was concentrated in vacuo, diluted with 1N HCl (20 ml) and heated under reflux for 2 h. Then the phthalhydrazide was filtered off and the filtrate was concentrated in vacuo. The residue was taken up in dichloromethane (150 ml), neutralized with triethylamine until pH 9, and a solution of ditertiobutyldicarbonate (5 g, 22 mmol) in dichloromethane (10 ml) was added. The mixture was heated under reflux overnight and, after usual work-up, the product was obtained by flash chromatography on silica gel (ethyl acetate:hexane; 25:75) (3 g, 75%).

Step C:
Cis-N-Tertiobutoxycarbonyl-2-Fluoro-4-Chloro-2-Butenyl-1-Amine

Mesylchloride (0.9 ml, 11 mmol) was added to a cold (0° C.) solution of cis-N-tertiobutoxycarbonyl-2-fluoro-4-hydroxy-3-butenyl-1-amine (2.05 g, 10 mmol) and triethylamine (1.6 ml, 11 mmol) in anhydrous dichloromethane (40 ml). The mixture was stirred overnight and, after usual work-up, the title compound cis-N-tertiobutoxycarbonyl-2-fluoro-4-chloro-2-butenyl-1-amine was obtained by flash chromatography on silica gel (ethyl acetate:hexane; 15:85) (1.7 g, 75%).

Step D:
Cis-5'-Deoxy-5'-(4-Tertiobutoxycarbonylamino-2-Fluoro-2-Butenyl)Methylamino-2',3'-Isopropylideneadenosine A solution of 5'-deoxy-5'-methylamino-2',3'-isopropylideneadenosine (1.65 g, 5 mmol), cis-N-tertiobutoxycarbonyl-2-fluoro-4-chloro-2-butenyl-1-amine (1.2 g, 4 mmol), potassium carbonate (0.7 g, 4 mmol) and sodium iodide (0.07 g, 0.5 mmol) in anhydrous acetonitrile (30 ml) was heated under reflux overnight. The mixture was concentrated in vacuo, diluted with ethyl acetate, washed with brine and dried over MgSO$_4$. the product was purified by flash chromatography on silica gel (diethylamine: chloroform; 2:98) (1.7 g, 70%).

Step E:
Cis-5'-Deoxy-5'-(4-Amino-2-Fluoro-2-Butenyl)Methylaminoadenosine

A suspension of cis-5'-deoxy-5'-(4-tertiobutoxycarbonylamino-2-fluoro-2-butenyl)methylamino-2',3'-isopropylideneadenosine in 1N sulphuric acid (5 ml) was stirred for 2 days at room temperature. Then the mixture was diluted with absolute ethanol (200 ml) and kept at 0° C. overnight. The precipitate was collected, dissolved in a minimum of water, and reprecipitated with absolute ethanol (200 ml). This procedure was repeated twice to give the title compound cis-5'-deoxy-5'-(4-amino-2-fluoro-2-butenyl)methylaminoadenosine (1 g, 75%; mp: 250°-260° C. decomposed).

EXAMPLE VIII

Preparation of 5'-Deoxy-5'-(3-Amino-2,2-Difluoropropyl)Methylaminoadenosine

Step A: Ethyl 2,2-Difluoro-3-Hydroxypropionate

A mixture of paraformaldehyde (4.5 g, 50 mmol), ethyl difluorobromoacetate (10.2 g, 50 mmol) and activated zinc dust (3.3 g, 40 mmol) in anhydrous tetrahydrofuran was heated under reflux for 0.5 h. Then the mixture was treated with a saturated aqueous solution of ammonium chloride and extracted with diethyl ether. After usual work-up the desired compound ethyl 2,2-difluoro-3-hydroxypropionate was obtained by flash chromatography on silica gel (ethyl acetate:hexane; 25:75) (4.1 g, 53%).

Step B: Ethyl 2,2-Difluoro-3-Tetrahydropyranyloxypropionate

Dihydropyrane (2 ml, 22 mmol) was added to a solution of ethyl 2,2-difluoro-3-hydroxypropionate (3.1 g, 20 mmol) and pyridinium p-toluenesulfonate (0.25 g, 1 mmol) in anhydrous dichloromethane (50 ml). The mixture was stirred overnight at room temperature and the desired compound ethyl 2,2-difluoro-3-tetrahydropyranyloxypropionate was obtained by flash chromatography on silica gel (ethyl acetate:hexane; 15:85) (4 g, 80%).

Step C: 2,2-Difluoro-3-Tetrahydropyranyloxy-1-Propanol

A solution of ethyl 2,2-difluoro-3-tetrahydropyranyloxypropionate (3.5 g, 15 mmol) in absolute ethanol (10 ml) was added dropwise to a slurry of sodium borohydride (0.57 g, 15 mmol) at room temperature in absolute ethanol (20 ml). Then the mixture was stirred an additional hour at room temperature. Then the mixture was concentrated in vacuo, hydrolyzed with aqueous ammonium chloride, extracted with ethyl acetate and dried over magnesium sulfate. The product was purified by flash chromatography on silica gel (ethyl acetate:hexane; 25:75) (2.7 g, 90%).

Step D: 2,2-Difluoro-3-Tetrahydropyranyloxypropyl Trifluoromethanesulfonate

Triflic anhydride (1.8 ml, 11 mmol) was added to a cold (0° C.) solution of 2,2-difluoro-3-tetrahydropyranyloxy-1-propanol 91.6 g, 10 mmol), pyridine (0.9 ml, 11 mmol) in anhydrous dichloromethane (50 ml). The mixture was stirred 1 h at 0° C. and, after usual work-up, the product was purified by flash chromatography on silica gel (ethyl acetate:hexane; 15:85) (2.6 g, 80%).

Step E: 2,2-Difluoro-3-Phthalimido-1-Tetrahydropyranyloxypropane

A mixture of 2,2-difluoro-3-tetrahydropyranyloxypropyl trifluoromethanesulfonate (2.3 g, 7 mmol), potassium phthalimide (1.4 g, 7.7 mmol) and anhydrous dimethylformamide (50 ml) under nitrogen was stirred and heated at 85° C. overnight. After cooling, salts are filtered off, and the solvent was removed in vacuo. The residue was taken up in dichloromethane (100 ml), washed with 0.5M NaOH (30 ml) and brine. The organic phase was separated, dried over magnesium sulfate and concentrated. The desired compound 2,2- difluoro-3-phthalimido-1-tetrahydropyranyloxypropane was purified by flash chromatography on silica gel (ethyl acetate:hexane; 20:80) (2 g, 90%).

Step F: 2,2-Difluoro-3-Phthalimido-1-Propanol

A solution of 2,2-difluoro-3-phthalimido-1-tetrahydropyranyloxypropane (2 g, 6.15 mmol), paratoluene sulfonic acid (0.1 g) in absolute ethanol was stirred overnight at room temperature. Then the mixture was concentrated in vacuo, diluted with ethyl acetate and washed with brine. The organic phase was separated, dried over magnesium sulfate and concentrated in vacuo. The crude alcohol 2,2-difluoro-3-phthalimido-1-propanol (1.4 g) was used for the next step without further purification.

Step G: 2,2-Difluoro-3-Phthalimido-Propyl Trifluoromethane Sulfonate

Triflic anhydride (1.1 ml, 6.6 mmol) was added to a cold (0° C.) solution of 2,2-difluoro-3-phthalimido-1-propanol (1.4 g, 6 mmol), pyridine (0.5 ml, 6.6 mmol) in anhydrous dichloromethane (30 ml). The mixture was stirred 1 h at 0° C. and, after usual work-up, the product was purified by flash chromatography on silica gel (ethyl acetate:hexane; 20:80) (1.7 g, 75%).

Step H:
5'-Deoxy-5'-(2,2-Difluoro-3-Phthalimido-Propyl)Methylamino-2',3'-Isopropylideneadenosine A mixture of 2,2-difluoro-3-phthalimido-propyl trifluoromethane sulfonate (1.5 g, 4 mmol), 5'-deoxy-5'-methylamino-2',3'-isopropylideneadenosine (1.2 g, 4.2 mmol) and triethylamine (0.55 ml, 4.2 mmol) in anhydrous dimethyl formamide was heated 2 days at 50° C. Then the mixture was concentrated in vacuo and the product was purified by flash chromatography on silica gel (diethylamine:chloroform; 2:98) (1.5 g, 75%).

Step I:
5'-Deoxy-5'-(2,2-Difluoro-3-Tertiobutoxycarbonylaminopropyl)-Methylamino-2',3'-Isopropylideneadenosine A mixture of 5'-deoxy-5'-(2,2-difluoro-3-phthalimidopropyl)methylamino-2',3'-isopropylideneadenosine (1.1 g, 2 mmol) in ethanol (10 ml) was heated under reflux overnight. Then the mixture was concentrated in vacuo, diluted with 1N acetic acid until pH 4 was reached, and cooled at 0° C. The precipitate was filtered off and the filtrate was neutralized until pH 9 with triethylamine and concentrated in vacuo. The residue was taken up in dichloromethane and ditertiobutyldicarbonate (0.45 g, 2 mmol) was added. The mixture was heated under reflux overnight and, after usual work-up, the product was purified by flash chromatography on silica gel (diethylamine:chloroform; 2:98) (0.8 g, 70%).

Step J:
5'-Deoxy-5'-(3-Amino-2,2-Difluoropropyl)Methylaminoadenosine

A suspension of 5'-deoxy-5'-(2,2-difluoro-3-tertiobutoxycarbonylaminopropyl)methylamino-2',3'-isopropylideneadenosine (0.8 g, 1.5 mmol) in 1N sulphuric acid (4 ml) was stirred 2 days at room temperature. Then the mixture was diluted with absolute ethanol (150 ml) and kept at 0° C. overnight. The precipitate was collected, dissolved in a minimum of water, and reprecipitated with absolute ethanol (150 ml). This procedure was repeated twice to give the title compound 5'-deoxy-5'-(3-amino-2,2-difluoropropyl)methylaminoadenosine (0.6 g, 80%: mp: 250°-260° C. decomposed).

EXAMPLE IX

Preparation of Cis-5'-Deoxy-5'-(4-Carboxy-3-Amino-2-Butenyl)Methylaminoadenosine Step A: 2-Amino-5-Hydroxy-3-Pentynoic Acid A mixture of glyoxylic acid monohydrate (23 g, 250 mmol), propargyl alcohol (16.8 g, 300 mmol), copper (II) chloride (3.2 g, 25 mmol) and ammonium acetate (49 g, 600 mmol) in ethanol (100 ml) is heated under reflux for 6 h. Then the reaction mixture is concentrated in vacuo, diluted with water (50 ml), acidified to pH 5 with 1N HCl and washed twice with ether (100 ml). Then the aqueous solution is poured on an ion exchange resin column (DOWEX 50, H+). The column is eluted with 1M ammonium hydroxide to give the title compound 2-amino-5-hydroxy-3-pentynoic acid.

Step B: Tertiobutyl-2-Amino-5-Hydroxy-3-Pentynoate

A suspension of 2-amino-5-hydroxy-3-pentynoic acid (12.5 g, 100 mmol) concentrated in sulphuric acid (2 ml) and isopropylene (50 ml) in a sealed Parr's flask is shaken 2 days at room temperature. The crude product, after evaporation of the excess of isopropylene, is used for the next step without further purification.

Step C:
Tertiobutyl-2-Tertiobutoxycarbonylamino-5-Hydroxy-3-Pentynoate

A solution of the crude tertiobutyl-2-amino-5-hydroxy-3-pentynoate (100 mmol), ditertiobutyldicarbonate (22 g, 100 mmol) and triethylamine (25 ml, 200 mmol) in chloroform is heated under reflux overnight. Then, after usual work-up, the product is purified by flash chromatography on silica gel (ethyl acetate:hexane; 20:80).

Step D:
Cis-Tertiobutyl-2-Tertiobutoxycarbonylamino-5-Hydroxy-3-Pentenoate

A solution of tertiobutyl-2-tertiobutoxycarbonylamino-5-hydroxy-3-pentynoate (13.6 g, 50 mmol) in ethanol (200 ml) is hydrogenated in presence of Lindlar catalyst (0.6 g) at atmospheric pressure and room temperature. In 3 h one equivalent of hydrogen (1.1 liters) is taken up. Then the catalyst is removed by filtration and the mixture is concentrated in vacuo which will yield a clear oil. The title compound is obtained by flash chromatography on silica gel (ethyl acetate:hexane; 15:85.

Step E:
Cis-Tertiobutyl-2-Tertiobutoxycarbonylamino-5-Chloro-3-Pentenoate

Mesyl chloride (0.9 ml, 11 mmol) is added to a cold (0° C.) solution of cis-tertiobutyl-2-tertiobutoxycarbonylamino-5-hydroxy-3-pentenoate (2.75 g, 10 mmol) and triethylamine (1.6 ml, 11 mmol) in anhydrous dichloromethane (50 ml). The mixture is stirred overnight and, after usual work-up, the title compound is purified by flash chromatography on silica gel (ethyl acetate:hexane; 20:80).

Step F:
Cis-5'-Deoxy-5'-(4-Tertiobutoxycarbonyl-3-Tertiobutoxycarbonylamino-2-Butenyl)Methylamino-2',3'-Isopropylideneadenosine A solution of cis-tertiobutyl-2-tertiobutoxycarbonylamino-5-chloro-3-pentenoate (1.5 g, 5 mmol), 5'-deoxy-5'-methylamino-2',3'-isopropylideneadenosine (1.6 g, 5 mmol) potassium carbonate (0.7 g, 5 mmol) and sodium iodide (0.8 g, 0.5 mol) in acetonitrile (30 ml) is heated under reflux overnight. After usual work-up, the product is purified by flash chromatography on silica gel (diethylamine:chloroform; 2:98).

Step G:
Cis-5'-Deoxy-5'-(4-Carboxy-3-Amino-2-Butenyl)Methylaminoadenosine

A suspension of cis-5'-deoxy-5'-(4-tertiobutoxycarbonyl-3-tertiobutoxycarbonylamino-2-butenyl)methylamino-2',3'-isopropylideneadenosine (1.5 g, 3 mmol) in 1N sulphuric acid (5 ml) is stirred 2 days at room temperature. Then the mixture is diluted with ethanol (200 ml) and kept at 0° C. overnight. The precipitate is collected, dissolved in a minimum amount of water, and reprecipitated with ethanol (200 ml). This procedure is repeated twice and will yield the title compound cis-5'-deoxy-5'-(4-carboxy-3-amino-2-butenyl)-methylaminoadenosine. (Usual work-up involves the extraction of the product from the aqueous phase by three extractions with the organic solvent (as in Step C, Example I) and the organic phase dried over magnesium sulfate, filtered off and concentrated in vacuo.)

The present invention provides a method of effecting immunosuppression, and more specifically, a method of suppressing cell-mediated immunity, in a patient in need thereof comprising administering to said patient an effective immunosuppressive amount of a compound of formula (1).

As used herein, the term "patient" refers to a warm-blooded animal such as a mammal which is suffering from a disease, such as an autoimmune disease or "graft versus host" disease, or is in danger of rejection of a transplanted allogeneic tissue or organ. It is understood that humans, mice and rats are included within the scope of the term "patient".

Administration of a compound of formula (1) to a patient results in an immunosuppressive effect in the patient. More specifically, administration of a compound of formula (1) to a patient results in suppression of cell-mediated immunity in the patient. In other words, by treatment of a patient with a compound of formula (1), the adaptive immune response of the patient and, more specifically, the cell-mediated adaptive immune response in the patient, is inhibited or suppressed over that present in the absence of treatment.

A patient is in need of treatment with an immunosuppressive agent, such as a compound of formula (1), where the patient is suffering from an autoimmune disease, "graft versus host" disease or in order to prevent rejection of transplanted allogeneic tissues or organs. The term "autoimmune disease" refers to those disease states and conditions wherein the immune response of the patient is directed against the patient's own constituents resulting in an undesireable and often terribly debilitating condition.

Patients suffering from autoimmune diseases such as rheumatoid arthritis, insulin-dependent diabetes mellitus, certain hemolytic anemias, rheumatic fever, thyroiditis, ulceractive colitis, myestheniagravis, glomerulonephritis, allergic encephalo-myelitis, continuing nerve and liver destruction which sometimes follows viral hepatitis, multiple sclerosis and systemic lupus erythematosus are in need of treatment with an immunosuppressive agent such as a compound of formula (1). Rheumatoid arthritis, insulin-dependent diabetes mellitus and multiple sclerosis are characterized as being the result of a cell-mediated autoimmune response and appear to be due to the action of T-cells. As such, treatment of patients suffering from these diseases by administration of a compound of formula (1) will be particularly effective in preventing further deterioration or worsening of the patient's condition. Treatment of a patient at an early stage of an autoimmune disease, such as rheumatoid arthritis, insulin-dependent diabetes mellitus or multiple sclerosis, would be particularly effective in preventing further deterioration of the disease state into a more serious condition. For example, insulin-dependent diabetes mellitus (IDDM) is an autoimmune disease which is believed to result from the autoimmune response directed against the $\beta$-cells of the islets of Langerhans which secrete insulin. Treatment of a patient suffering from an early stage of IDDM prior to the complete destruction of the $\beta$-cells of the islets of Langerhans would be particularly useful in preventing further progression of the disease since it would prevent or inhibit further destruction of remaining insulin-secreting $\beta$-cells. It is understood that treatment of a patient suffering from an early stage of other autoimmune diseases will also be particularly useful to prevent or inhibit further natural progression of the disease state to more serious stages.

Patients who have received or who are about to receive an allogeneic tissue or organ transplant, such as an allogeneic kidney, liver, heart, skin, bone marrow, are also patients who are in need of prophylactic treatment with an immunosuppressive agent such as a compound of formula (1). An immunosuppressive agent will prevent the cell-mediated immune response of the donee from rejecting the allogeneic tissue or organ of the donor. Likewise, patients suffering from "graft versus host" disease are patients who are in need of treatment with an immunosuppressive agent such as a compound of formula (1). An immunosuppressive agent will prevent the cell-mediated immune response of the transplanted tissue or organ from rejecting the allogeneic tissue or organ of the donee.

Based on standard clinical and laboratory tests and procedures, an attending diagnostician, as a person skilled in the art, can readily identify those patients who are in need of treatment with an immunosuppressive agent such as a compound of formula (1).

An effective immunosuppressive amount of a compound of formula (1) is that amount which is effective, upon single or multiple dose administration to a patient, in providing an immunosuppressive effect or, more particularly, a cell-mediated immunosuppressive effect. An immunosuppressive effect refers to the slowing, interrupting, inhibiting or preventing the further expression of the immune response or of the cell-mediated immune response.

An effective immunosuppressive amount of a compound of formula (1) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective immunosuppressive amount of a compound of formula (1) is expected to vary from about 1000 milligram per kilogram of body weight per day (mg/kg/day) to about 1 mg/kg/day. Preferred amounts are expected to vary from about 10 to about 100 mg/kg/day.

In effecting treatment of a patient, a compound of formula (1) can be administered in any form or mode which makes the compound bioavailable in effective amounts, including oral and parenteral routes. For example, compounds of formula (1) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of formula (1), while effective themselves, may be formulated and administered in the form of their pharmaceutically acceptable acid addition salts for purposes of stability, convenience of crystallization, increased solubility and the like.

A compound of formula (1) may be administered in the form of a pharmaceutical composition comprising an effective immunosuppressive amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel TM, corn starch and the like; lubricants such as magnesium stearate or Sterotex TM; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of formula (1) may be incorporated into a solution or suspension. These preparations should contain at least 0.1% of a compound of the invention, but may be varied to be between 0.1 and about 50% of the weight thereof. The amount of the compound present in such compositions should be such that a suitable dosage will be obtained. Preferred compositions and preparations are prepared so that a parenteral dosage unit contains between 5.0 to 100 milligrams of the compound of formula (1).

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of the formula (1) in the method of use of the present invention. In general, compounds of formula (1) wherein Q is of the formula (Ia), (Ic) or (Ie) are preferred with those compounds wherein Q is of the formula (Ie) being especially preferred. Among those compounds of formula (1) wherein Q is of the formula (Ie), those having a cis-configuration are particularly preferred.

The following list identifies compounds of the formula (1) which are particularly preferred embodiments of the present invention:

(cis)-5'-deoxy-5'-[(4-amino-2-butenyl)methylamino]adenosine, (cis)-5'-deoxy-5'-[(4-amino-2- butenyl)amino]adenosine and their 2-fluoro, 3-fluoro and 2,3-difluoro analogs; 5'-deoxy-5'-[(3-amino-2-methylenepropyl)methylamino]adenosine, 5'-deoxy-5'-[(3-amino-2-methylenepropyl)amino]adenosine and their mono and difluoro analogs (X and/or Y of Ia are fluoro); (cis)-5'-deoxy-5'-[(4-amino-4-carboxy-2-butenyl)methylamino]adenosine and (cis)-5'-deoxy-5'-[(4-amino-4-carboxy-2-butenyl)amino]adenosine.

The following example illustrates the method of use of the compounds of formula (1) according to the present invention. This example is understood to be illustrative only and is not intended to limit the scope of the invention in any way. As used herein the following terms have the indicated meanings: "[$^3$H]-TdR" refers to tritiated thymidine; "Units" refers to units of interleukin-2; "$\mu$M" refers to micromolar; "CPM" refers to counts per minute.

EXAMPLE X

Inhibition of Interleukin-2 Dependent T-Cell Growth In Vitro

Inhibition of interleukin-2 (IL-2) dependent T-cell growth in vitro was determined essentially as described by Bowlin et al. [*Cell Immunol.* 98, 341–50 (1986)]. Cloned IL-2 dependent cytolytic T lymphocytes (CTLL-20), incubated alone or in the presence of (cis)-5'-deoxy-5'-[(4-amino-2-butenyl)methylamino]adenosine (Compound A) at varying concentrations, were stimulated with 10 Units/mL of IL-2 and were grown in culture. After 72 hours, cell counts were determined based on trypan blue exclusion.

The CTLL-20 cells were restimulated with IL-2 (10 units/mL) for 24 hours and were pulsed for the final 6 hours with [$^3$H]-TdR to measure DNA synthesis activity essentially as described by Bowlin et al. [*Cell Immunol.* 98, 341–50 (1986)].

The results of this study are presented in Table 1.

TABLE 1

INHIBITION OF INTERLEUKIN-2 DEPENDENT T-CELL GROWTH in vitro

| Treatment Group | Compound A ($\mu$M) | Cell Count Number Recovered (% Reduction over Group 1) | DNA Synthesis CPM (% Reduction over Group 1) |
|---|---|---|---|
| 1 | 0 (Control) | $6.6 \times 10^6$ | 33541 |
| 2 | 100 | $1.0 \times 10^6$ (85%) | 8114 (76%) |
| 3 | 10 | $2.0 \times 10^6$ (70%) | 10005 (70%) |
| 4 | 1 | $4.0 \times 10^6$ (39%) | 19218 (43%) |

Compound A = (cis)-5'-deoxy-5'-[(4-amino-2-butenyl) methylamino]adenosine

EXAMPLE XI

Time Course of Inhibition of Interleukin-2 Dependent T-Cell Growth In Vitro

Inhibition of interleukin-2 (IL-2) dependent T-cell growth in vitro was determined essentially as described in Example X. Cloned IL-2 dependent cytolytic T lymphocytes (CTLL-20), incubated alone or in the presence of (cis)-5'-deoxy-5'-[(4-amino-2-butenyl)methylamino]adenosine (Compound A) at 100 $\mu$M, were stimulated with 10 Units/mL of IL-2 and were grown in culture for 1, 2, 3 or 4 days. At the end of incubation, cell counts were determined based on trypan blue exclusion.

The CTLL-20 cells were then restimulated with IL-2 (10 units/mL) for 24 hours and were pulsed for the final 6 hours with [$^3$H]-TdR to measure DNA synthesis activity essentially as described for Example X.

The results of this study are presented in Table 2.

TABLE 2

TIME COURSE OF INHIBITION OF INTERLEUKIN-2 DEPENDENT T-CELL GROWTH in vitro

| Incubation Time Days | Compound A ($\mu$M) | Cell Count Number Recovered (% Reduction over Control) | DNA Synthesis CPM (% Reduction over Control) |
|---|---|---|---|
| 1 | 0 (Control) | $0.5 \times 10^6$ | 18598 |
| 1 | 100 | $0.3 \times 10^6$ (40) | 7622 (59) |
| 2 | 0 (Control) | $3.2 \times 10^6$ | 11193 |
| 2 | 100 | $0.7 \times 10^6$ (78) | 6197 (45) |
| 3 | 0 (Control) | $6.6 \times 10^6$ | 33541 |
| 3 | 100 | $1.0 \times 10^6$ (85%) | 8114 (76%) |
| 4 | 0 (Control) | $4.7 \times 10^6$ | 32522 |
| 4 | 100 | $1.7 \times 10^6$ (64%) | 8863 (73) |

Compound A = (cis)-5'-deoxy-5'-[(4-amino-2-butenyl) methylamino]adenosine

What is claimed is:

1. A method of effecting immunosuppression in a patient in need thereof comprising administering to said patient an effective immunosuppressive amount of a compound of the formula $$\text{(1)}$$

wherein
R represents H, methyl or ethyl and
Q represents a radical of formulae Ia to If depicted as follows:

(Ia) $H_2N-\underset{V_2}{\underset{|}{C}}-\underset{\|}{\overset{X \diagdown \diagup Y}{C}}-CH_2-$ (Ib) $H_2N-\underset{V_2}{\underset{|}{C}}-C\equiv C-CH_2-$ (Ic) $\underset{V_2}{\overset{H_2N\diagdown}{\diagup}}\underset{W\ \ Z}{\overset{(CH_2)_n}{\diagup}}CH-$ (Id) $H_2N-\underset{V_2}{\underset{|}{C}}-\underset{F}{\underset{|}{C}}-CH_2-$ (Ie) $H_2N-\underset{V_2\ W}{\underset{|\ \ |}{C}}-CH=CH-CH_2-$ (If) $H_2N-CH_2-CH_2-\underset{Z}{\underset{|}{C}}-CH_2-$ wherein
$R_1$ is H or F, n is an integer 1 or 2,
V$_1$ is H or methyl,
V$_2$ is H or COOH, and
W, X, Y and Z are each independently H, F, Cl or Br;

or a pharmaceutically acceptable salt thereof.

2. A method according to claim 1 wherein the immunosuppression is a suppression of cell-mediated immunity.

3. A method according to claim 2 wherein the patient is in need of treatment for allograft rejection.

4. A method according to claim 2 wherein the patient is in need of treatment for an autoimmune disease.

5. A method according to claim 4 wherein the autoimmune disease is insulin-dependent diabetes mellitus.

6. A method according to claim 4 wherein the autoimmune disease is multiple sclerosis.

7. A method according to claim 4 wherein the autoimmune disease is rheumatoid arthritis.

8. A method according to claim 1 wherein the compound is (cis)-5'-deoxy-5'-[(4-amino-2-butenyl)methylamino]adenosine.

* * * * *

UNITED STATES PATENT AND TRADEMARK OFFICE
CERTIFICATE OF CORRECTION

PATENT NO. : 5,308,837
DATED : May 3, 1994
INVENTOR(S) : Terry L. Bowlin

It is certified that error appears in the above-identified patent and that said Letters Patent is hereby corrected as shown below:

At column 1, line 66, the patent reads "phagocytosis macrophages" and should read "phagocytosis by macrophages".

At column 16, line 53, the patent reads "-2Fluoro" and should read "-2-Fluoro".

Signed and Sealed this

Fourteenth Day of February, 1995

Attest:

BRUCE LEHMAN

Attesting Officer        Commissioner of Patents and Trademarks